United States Patent
Ettl et al.

(10) Patent No.: US 7,078,569 B2
(45) Date of Patent: Jul. 18, 2006

(54) METHOD FOR PRODUCING ALKYLKETEN DIMERS

(75) Inventors: Roland Ettl, Hassloch (DE); Manfred Winter, Dittelsheim-Hessloch (DE); Torsten Freund, Limburgerhof (DE); Thomas Kessler, Schifferstadt (DE); Guenther Grimm, Bruessel (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 91 days.

(21) Appl. No.: 10/495,756

(22) PCT Filed: Nov. 19, 2002

(86) PCT No.: PCT/EP02/12932

§ 371 (c)(1),
(2), (4) Date: May 27, 2004

(87) PCT Pub. No.: WO03/045936

PCT Pub. Date: Jun. 5, 2003

(65) Prior Publication Data

US 2005/0107639 A1    May 19, 2005

(30) Foreign Application Priority Data

Nov. 30, 2001 (DE) ................ 101 58 661

(51) Int. Cl.
*C07C 45/89* (2006.01)
(52) U.S. Cl. ...................................... 568/301
(58) Field of Classification Search .......... None
See application file for complete search history.

(56) References Cited

FOREIGN PATENT DOCUMENTS

| | | |
|---|---|---|
| DE | 34 34 212 | 3/1986 |
| EP | 0 550 107 | 7/1993 |
| EP | 0 612 739 | 8/1994 |
| EP | 0 741 121 | 11/1996 |
| WO | 94/19306 | 9/1994 |

*Primary Examiner*—Brian Davis
(74) *Attorney, Agent, or Firm*—Oblon, Spivak, McClelland, Maier & Neustadt, P.C.

(57) ABSTRACT

Alkylketene dimers are prepared by reacting acyl chlorides with tertiary amines in a molar ratio of from 1:1 to 1:1.6 at from 65 to 150° C. and with a residence time of from 1 to 30 minutes in the absence of solvents with thorough mixing and isolation of the alkylketene dimers.

8 Claims, No Drawings

METHOD FOR PRODUCING ALKYLKETEN DIMERS

This application is a 371 of PCT/EP02/12932 filed Nov. 19, 2002.

The present invention relates to a process for the preparation of alkylketene dimers by reacting acyl chlorides with tertiary amines in the absence of solvents with thorough mixing and isolation of the alkylketene dimers from the reaction mixture.

EP-A-0550107 discloses a process for the preparation of alkylketene dimers by reacting acyl chlorides with triethylamine in the absence of solvents. The acyl chloride is fed, with thorough mixing, into the triethylamine at a rate of not more than 3 mol per hour per mol of triethylamine, the mixing, the feed rate and the heat exchange being regulated in such a way that the viscosity of the mixture is kept at less than 250 mPa.s, measured at 60° C. (shear rate greater than sec$^{-1}$). The excess amine is then extracted from the reaction mixture with treatment with dilute hydrochloric acid. The reaction is carried out at from 50 to 100° C., preferably from 55 to 65° C.

EP-A-0612739 likewise discloses a process for the preparation of alkylketene dimers by reacting fatty acid halides with tertiary amines. In this process, at least 1.15 mol of tertiary amine are used per mol of fatty acid halide and the reaction is carried out in the presence of not more than 10% by weight, based on the amount of fatty acid halides, of an additional solvent. The alkylketene dimer is obtained by stripping of the tertiary amine and subsequent extraction with dilute acids.

EP-A-0684940 likewise discloses a process for the preparation of alkylketene dimers from acyl halides and tertiary amines. The reaction is carried out batchwise in the presence of a starting reaction mixture which contains alkylketene dimer and prepared crystals of a hydrohalide of a tertiary amine and in the presence of not more than 10% by weight, based on the fatty acid halides, of a solvent.

EP-A-0741121 discloses the preparation of alkylketene dimers by reacting fatty acid halides with tertiary amines in inert organic solvents. In order to work up the reaction mixture, the inert organic solvent is first distilled off for the most part, water or steam is then added and distillation is continued. The alkylketene dimers thus obtainable contain only small amounts of residual solvent and have, as a rule, alkylketene dimer contents of about 90% by weight. Even a small amount of residual solvent in alkylketene dimers is disadvantageous for many applications.

It is an object of the present invention to prepare solvent-free alkylketene dimers in a high space-time yield and with an alkylketene dimer content of at least 89% by weight.

We have found that this object is achieved, according to the invention, by a process for the preparation of alkylketene dimers by reacting acyl chlorides with tertiary amines in the absence of solvents with thorough mixing and isolation of the alkylketene dimers from the reaction mixture, if acyl chlorides and tertiary amines are reacted in a molar ratio of from 1:1 to 1:1.6 at from 65 to 150° C. and with a residence time of from 1 to 30 minutes.

While the alkylketene dimer formed in the reaction is liquid under the reaction conditions, the salts formed in the reaction are virtually insoluble in the reaction mixture and lead to a considerable increase in the viscosity of the mixture. Thus, the viscosities of the reaction mixture at 60° C. are, for example, from 300 mPa.s to 100 Pa.s (measured in a Physica rotational viscometer). The viscosity of the reaction mixture is preferably from 500 to 8000 mPa.s.

Alkylketene dimers can be characterized, for example, with the aid of the formula

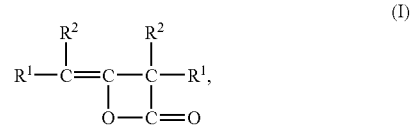

where
$R^1$ is $C_4$- to $C_{30}$-alkyl or $C_4$- to $C_{30}$-alkenyl and
$R^2$ is hydrogen or $C_1$- to $C_8$-alkyl
it being possible for the alkyl radicals $R^1$ and, if $R^2$ is alkyl, $R^2$ each to be linear or branched. The acyl chlorides used in the reaction are, for example, of the formula

where $R^1$ and $R^2$ have the meanings stated in formula I. The acyl chlorides II preferably have 14 to 22 carbon atoms. Mixtures of different acyl chlorides may also be used. Examples of mixtures which are of industrial importance are those which are obtainable by chlorinating naturally occurring fatty acids, such as acid chlorides based on fatty acids which are obtained from coconut oil, tall oil, castor oil, olive oil, beef tallow or palm kernel oil. Typical examples of acid chlorides are myristyl chloride, palmityl chloride, stearyl chloride, behenyl chloride, oleyl chloride and isostearyl chloride.

Tertiary amines which may be used are monoamines or diamines having at least one methyl group. Monoamines of the formula

where $R^1$, $R^2$ and $R^3$, independently of one another, are $C_1$- to $C_6$-alkyl, $C_2$- to $C_6$-alkenyl or $C_5$- or $C_6$-cycloalkyl or $R^1$ and $R^2$ are linked via an alkylene chain of up to 6, preferably 4 or 5, carbon atoms, are preferred. Examples of monoamines are dimethylcyclohexylamine, diethylmethylamine, dimethylethylamine, trimethylamine, triethylamine, dimethylisopropylamine, N-methylpiperidine, N-methylpyrrolidine, dimethylbutylamine and dimethyl-2-ethylhexylamine. Examples of diamines are N,N,N',N'-tetramethylpropanediamine, N,N,N',N'-tetramethylhexanediamine and N,N-dimethyl-N',N'-diethylpropanediamine. Mixtures of monoamines and diamines are possible. Preferably used tertiary amines are dimethylcyclohexylamine, dimethylisopropyl-amine, dimethylethylamine and N-methylpiperidine.

Acyl chlorides and tertiary amines are reacted in a molar ratio of from 1:1 to 1:1.16, preferably from 1:1 to 1:1.25, particularly preferably from 1:1.02 to 1:1.10. The reaction is carried out at from 65 to 150° C., preferably from 70 to 110° C., in particular from 80 to 110° C. The reactants are thoroughly mixed, for example in static or dynamic mixers, for example in pumps, extruders, kneaders or nozzles. For example, acyl chloride, and tertiary amines can each be metered separately from one another, the reactants then mixed with one another and the reaction mixture conveyed with the aid of pumps, kneaders or extruders.

Acyl chlorides and tertiary amines can, for example, also be sprayed and mixed in a multimedium nozzle. The reaction of acyl chlorides and tertiary amines takes place very rapidly and is therefore complete within minutes. On spraying, finely divided product streams of tertiary amines and acyl chlorides are obtained. The mean particle diameter of the sprayed reactants is, for example, from 1 μm to 1000 μm, preferably from 10 μm to 100 μm. With the aid of suitable cooling units, the reaction temperature is kept in the abovementioned range. It is possible to use, for example, reactors which ensure thorough mixing of the reactants and which have a large heat exchange surface, for example a loop reactor with heat exchanger or planetary roller extruder. A further possibility for removing the heat of reaction from the reaction zone is by evaporative cooling. Here, the tertiary amine, being the more readily volatile component, vaporizes and is fed back into the process after condensation. The reaction can be carried out at atmospheric, reduced or superatmospheric pressure, for example, at from 50 mbar abs. to 100 bar abs., preferably from 50 mbar abs. to 10 bar abs. If, for example, a tubular reactor with external backmixing is used, the reaction can be carried out, for example, at from atmospheric pressure to 100 bar abs., preferably from atmospheric pressure to 10 bar abs. In a continuous procedure in a kneader, for example, it is possible to work in a range of from 50 mbar abs. to 10 bar abs. and with the use of evaporative cooling.

The reaction of the acyl chlorides with the tertiary amines is preferably carried out continuously. Suitable apparatuses for this purpose are, for example, tubular reactors with or without internals which serve for mixing and/or heat removal, continuously operating kneaders or tubular reactors which have a mixing nozzle and a conveying means. The reactors must also have suitable heat exchangers. The residence time in the reaction zone is, for example, from 1 to 30, preferably from 1 to 15, minutes.

The reaction of the tertiary amines with the acyl chlorides particularly preferably takes place by continuous feeding of the reactants separately from one another into continuously operated extruders, for example a twin-screw extruder or a planetary roller extruder, at from 70 to 120° C., preferably from 90 to 110° C. Dimethylisopropylamine, dimethylethylamine, dimethylcyclohexylamine, N-methylmorpholine and triethylamine are particularly preferably used as the amine component for this purpose.

After the end of the reaction, the reaction mixture is worked up in a conventional manner, for example with the aid of physical methods, such as centrifuging, or by dissolving the ammonium salts in water or in dilute acids. This is effected, for example, by using dilute acids, for example dilute sulfuric acid (concentration from about 2 to 20% by weight), to extract the ammonium salts formed in the reaction. Here, excess amine as ammonium salt, together with the ammonium salts formed in the reaction, are dissolved in the aqueous phase and separated off. In an expedient procedure, the reaction slurry is introduced into a kettle which is provided with a stirrer and in which dilute sulfuric acid which is at from 65 to 90° C., preferably from 70 to 80° C., is initially taken. A preferred variant of the working-up of the reaction slurry employs a dynamic mixer into which the slurry is conveyed perpendicularly onto the rotating axle.

After the phase separation, the alkylketene dimer isolated is preferably subjected to a further extraction with water in a mixer-settler apparatus.

Alkylketene dimers having a diketene content of at least 89% by weight remain. In most cases, the diketene content is at least 90% by weight.

The diketenes obtainable by the novel process are used as water repellents. The most important application of these compounds is for the engine sizing of paper. For this purpose, alkylketene dimers dispersed in water with the aid of protective colloids are added to the paper stock before the drainage. The amounts usually used are from 0.05 to 0.20% by weight, based on dry paper stock.

The lactone content stated in the examples is the content of alkylketene dimer of the formula I in % by weight. The residence time stated is an average residence time which was measured by suitable methods (e.g. concentration of a dye).

EXAMPLE 1

The reaction is carried out in a tubular reactor which consists of a double-walled tube having a total length of 100 cm and an internal diameter of 5 cm. The tubular reactor is equipped with an intensive mixer passing close to the wall. The reactor volume is 122 ml. Two inlet nozzles are present at the reactor entrance. In the middle of the reactor is a further nozzle for additional discharge of starting material or for sampling. The reactor contains three temperature measuring points distributed over the length and a discharge nozzle at the end. The intensive mixer is designed in such a way that thorough mixing of the two reactants takes place at the metering point of tertiary amine and acyl chloride and conveying of the reaction mixture to the reactor exit takes place, in addition to mixing, in the further course of the reactor. The temperature of the reactor is controled by means of a heating/cooling circulation. The reaction discharge is worked up either batchwise in a stirred apparatus or, preferably, continuously (conventionally by acid, aqueous extraction). In the batchwise working-up, a sample of the reaction discharge is stirred into dilute sulfuric acid at 65° C. After standing for 30 minutes, a phase separation occurs. The aqueous phase is discharged. The organic phase is mixed with water again and stirred for 15 minutes at 65° C. After the phase separation, the organic phase is separated off and is investigated by IR spectroscopy.

In the continuous working-up, the total reaction discharge is fed directly into a two-stage mixer-settler apparatus and the ammonium salts are extracted at from 65 to 70° C. with water which is acidified with acids (e.g. $H_2SO_4$ or HCl).

The reaction is started by simultaneously metering stearyl chloride, and dimethylcyclohexylamine into the reactor via the inlet nozzles with the aid of two pumps. The residence time of the reaction mixture in the reactor can be established with the aid of the metering rate. In a standard procedure, 453 g (1.5 mol) of stearyl chloride per hour and 209 g (1.65 mol) of dimethylcyclohexylamine per hour are metered via the separate inlet nozzle into the upper part of the reactor. The housing temperature is 60° C. As a result of the heat of reaction evolved, the internal temperature of the reaction mixture increases to 68 to 71° C. (the measuring point is located in the immediate vicinity of the metering point) and settles at this level. After a residence time of about 10 minutes, the producer emerges at the lower end of the reactor. The temperature level over the entire reactor is 66° C. at the reactor exit and 71° C. at the metering point. After continuous operation for 2 hours, a sample of the reaction discharge is taken and is worked up batchwise by stirring the reaction mixture with dilute sulfuric acid for 15 minutes at 65° C. After standing for 30 minutes, a phase separation occurs. The organic phase is extracted again with water and phase separation is allowed to take place. The aqueous phase is discharged and the organic phase is investigated by IR spectroscopy. A lactone content of 90.8% is determined.

EXAMPLE 2

The tubular reactor described in example 1 is used and is fed in each case with 906 g (3 mol) of stearyl chloride and 406 g (3.2 mol) of dimethycyclohexylamine per hour via the inlet nozzles. The starting materials are metered by means of 2 balances. The housing temperature of the reactor is 60° C. Owing to the heat of reaction, the temperature of the reaction mixture increases to 75 to 79° C. and decreases to 70 to 72° C. toward the reactor exit. After a residence time of about 5 minutes, the reaction product is discharged via the outlet nozzle of the reactor. The aqueous extraction of the resulting amine hydrochloride is effected in a mixer-settler apparatus connected to said reactor. The stearyldiketene separates as the upper phase and is removed continuously. The IR spectroscopic analysis gave a lactone content of 92.7% when a sample was taken after continuous operation for 3.5 hours.

EXAMPLE 3

The reactor used is a kneader which is equipped with heatable, internal shafts. The internal volume of the reactor is 0.47 l. The shafts and the housing of the kneader can be heated separately by means of external heating/cooling circulations. The two reactants are metered via a common inlet nozzle, and the acid chloride and the amine being premixed by means of a mixing nozzle and being metered directly into the reactor. The temperature of the reaction mixture is measured by means of thermocouples sealed in the reactor wall. The reactor is preheated to 60° C. and the internal shafts to 52° C. In each case 825 g of dimethylcyclohexylamine and 1 750 g of tallow fatty acid chloride are metered per hour into the reactor via the mixing nozzle. The average residence time of the reaction mixture in the reactor is 9.5 minutes. The reaction mixture is at a temperature of from 78 to 79° C. on entering the reactor and a temperature of 71 to 73° C. at the reactor exit. The reaction product is worked up as described in example 1. It has a lactone content of 90.0%.

EXAMPLE 4

The kneader described in example 3 is used but the housing temperature and the temperature of the internal shafts are adjusted to 75° C. The reactor is operated continuously by pumping in each case 1 167 g of N-methylpiperidine and 3 185 g of tallow fatty acid chloride per hour into the reactor. The temperature of the reaction mixture increases to 94 to 97° C. It is 88° C. at the reactor exit. The reaction mixture is worked up as described in example 1. The alkylketene dimer has a lactone content of 90.1%.

EXAMPLE 5

The reactor described in example 3 is used but the housing temperature is adjusted to 70° C. and the temperature of the internal shafts is adjusted to 55° C. The reactor is operated continuously by feeding it continuously with 1 167 g of N-methylpiperidine and simultaneously 3 185 g of tallow fatty acid chloride per hour. The internal temperature of the reaction mixture is from 84 to 87° C. at the reactor entrance and about 79° C. at the reactor exit, and the average residence time is about 5.5 minutes. The reaction mixture is worked up as described in example 1. The alkylketene dimer has a lactone content of 92.5%

EXAMPLE 6

The reactor consists of a mixing nozzle, a circular double-walled tube (internal diameter 9 mm) and a pump. The mixing nozzle is mounted in such a way that the two starting materials are mixed in the immediate vicinity of the pump and then further conveyed to the pump. Another double-walled, straight tube (internal diameter 9 mm) is mounted as a branch on the first circular tube in a manner such that the two reactants must first pass through the pump and the circular tubular reactor before they can enter the straight tube. The pump installed in the circular tubular reactor has a controllable delivery of from 2 to 20 kg/h.

The entire reactor is equipped with three temperature measuring points and two measuring points for pressure measurement. The temperature is controlled by means of two heating circulations which can be regulated independently of one another. The total reactor volume determined is 102 ml, including 65 ml in the circular reactor and 37 ml in the straight tube. The temperature of the heating circulation for the circular tubular reactor is adjusted to 60° C. and the temperature for the straight tubular reactor is adjusted to 66° C.

The reaction is started by simultaneously metering 186 g of dimethylisopropylamine/h and 584 g of tallow fatty acid chloride/h via the mixing nozzle into the circular tubular reactor. The internal temperature in this reactor section increases rapidly to 76 to 80° C. and settles at this value. After a residence time of about 7 minutes, the product emerges at the end of the reactor and, after adjustment of the pH, can be worked up in a conventional manner by aqueous extraction. The temperature in the second reactor section settles at from 71 to 72° C.; 70° C. are measured in the reactor discharge. After the discharge has been worked up, a lactone content of 92.1% is measured by IR spectroscopy.

EXAMPLE 7

The reactor described in example 7 is used. The temperature of the heating circulation for the circular tubular reactor is adjusted to 60° C. and the temperature for the straight tubular reactor is adjusted to 95° C.

The reaction is started by simultaneously metering 186 g of dimethylisopropylamine/h and 584 g of tallow fatty acid chloride/h via the mixing nozzle into the circular tubular reactor. The internal temperature in this reactor section increases rapidly to 76 to 80° C. and settles at this value. After a residence time of about 7 minutes, the product emerges at the end of the reactor and, after adjustment of the pH, can be worked up in a conventional manner by aqueous extraction. The temperature in the second reactor section settles at from 87 to 90° C. A temperature of 88° C. is measured at the reactor exit. After the discharge has been worked up, a lactone content of 90.4% is measured by IR spectroscopy in the upper phase separated off.

EXAMPLE 8

A twin-screw extruder having a free volume of 1.2 dm$^3$ was heated to 90° C. Tallow fatty acid chloride (TFACl) and dimethylisopropylamine (DMiPA) were metered into this apparatus by means of two pumps at the mass flow rates stated in table 1. As a result of the exothermic reaction, internal temperatures of from 95 to 106° C. were established. The reaction discharge was worked up continuously by mixing the reaction slurry with 0.362 times the mass flow rate of 10.6% strength sulfuric acid in a dynamic mixer which was connected directly to the extruder. The solid dimethylisopropylammonium hydrochloride dissolved in the aqueous phase. Two liquid phases were obtained. Thereafter, the melt of the ketene dimer was separated from the acidic solution of the ammonium salt and was washed twice with water at 75° C. in a continuously operating mixer-settler cascade. The β-lactone contents of the ketene dimers are shown in table 1.

TABLE 1

| Example | TFACl [kg/h] | DMiPA [kg/h] | β-Lactone [%] |
|---|---|---|---|
| 8a | 12.60 | 4.32 | 93.1 |
| 8b | 15.75 | 5.40 | 90.6 |
| 8c | 18.90 | 6.48 | 90.6 |
| 8d | 22.06 | 7.56 | 91.3 |

EXAMPLE 9

A planetary roller extruder having a free volume of 1.7 dm³ and consisting of two shots which were equipped with 6 mixer elements was heated by means of an external medium in the respective shots. Tallow fatty acid chloride (TFACl) and dimethylisopropylamine (DMiPA) were metered into this apparatus by means of two pumps in the ratio stated in table 2. The reaction discharge was worked up batchwise by mixing the reaction slurry with 0.362 times the mass of 10.6% strength sulfuric acid in a stirred container. The solid dimethylisopropylammonium hydrochloride dissolved in the aqueous phase. Two liquid phases were obtained. Thereafter, the melt of the ketene dimer was separated from the acidic solution of the ammonium salt and was washed twice with water at 75° C. The β-lactone contents of the ketene dimers are shown in table 2.

TABLE 2

| Experiment | Ratio mol of amine/mol of TFACl | Throughput kg/h | Temp ° C. Shot 1 | Temp ° C. Shot 2 | IR analysis Mean values Lactone % |
|---|---|---|---|---|---|
| 9a | 1.122 | 39.0 | 60 | 80.0 | 92.2 |
| 9b | 1.127 | 51.5 | 70 | 72.5 | 93.3 |
| 9c | 1.121 | 42.4 | 80 | 65.0 | 92.9 |
| 9d | 1.121 | 25.5 | 80 | 80.0 | 92.8 |
| 9e | 1.171 | 32.2 | 90 | 87.5 | 91.1 |
| 9f | 1.122 | 42.6 | 100 | 80.0 | 89.3 |
| 9g | 1.0575 | 40.0 | 90 | 80 | 91.7 |
| 9h | 1.105 | 40.0 | 90 | 80 | 92.8 |
| 9i | 1.105 | 40.0 | 90 | 80 | 93.6 |
| 9k | 1.2 | 40.0 | 70 | 80 | 93.3 |

Examples 9a–9f were carried out using dimethylisopropylamine and examples 9g–9k using dimethylethylamine.

EXAMPLE 10

Comparison of the paper sizing of an alkylketene dimer prepared according to the invention with a commercial alkylketene dimer The alkylketene dimer prepared according to example 1 (a) was melted at 70° C. and dispersed in a solution of 0.1% of ligninsulfonate as a dispersant, 2% of cationic starch and water (to 100%) by means of an Ultraturrax stirrer at 80° C., with a ketene dimer content of 6%. The crude emission was homogenized twice by means of a high-pressure homogenizer (APV) at 200 bar and was cooled to 20° C. The AKD dispersion thus obtained was added to an experimental paper machine in the concentrations which are shown in table 3 and are based on dry paper stock. The paper stock contained 30% by weight of pine sulfate, 70% by weight of beech sulfate and 20% by weight of $CaCO_3$ (Hydrocarb® OG from Omya). The hydrophobic character of the resulting papers having a basis weight of 80 g/m² was determined by means of the Cobb 60s value and the HST value.

Determination of the degree of sizing (HST value) using the Hercules sizing tester:

The paper sample is clamped in the holder, 10 ml of the test ink are poured onto the sample and the measurement is started. When the chosen end point of the reflectance is reached, the time counter stops. The time is noted and the penetration time is stated in seconds.

Comparative Example 1

For comparison, an aqueous dispersion containing 6% of alkylketene dimer was likewise prepared from a commercial alkylketene dimer (Basoplast® 20 concentrated, lactone content 85%) by the method described above and was tested as a size as described above.

TABLE 3

| Alkylketene dimer prepared according to | Sizing determined according to | Amount of alkylketene dimer, based on dry paper stock [% by weight] | | | | | |
|---|---|---|---|---|---|---|---|
| | | 0.06 | 0.072 | 0.084 | 0.096 | 0.108 | 0.12 |
| Example 1c | Cobb 60 s | 60 | 47 | 32 | 29 | 25 | 24 |
| Comp. ex. 1 | Cobb 60 s | 72 | 67 | 44 | 30 | 26 | 25 |
| Example 1c | HST | 9 | 12 | 40 | 71 | 126 | 163 |
| Comp. ex. 1 | HST | 2 | 6 | 37 | 62 | 118 | 124 |

Comparative Example 2

580 g of dry toluene and 279 g (2.20 mol) of dried dimethylcyclohexylamine are initially taken in a double-walled 2 l stirred apparatus equipped with a stirrer passing close to the wall, a thermocouple and a metering apparatus and are heated to 50° C. After the internal temperature of 50° C. has been reached, 584 g (2.00 mol) of tallow fatty acid chloride ($C_{16}/C_{18}$ mixture) are pumped into the reactor with thorough stirring from a container standing on a balance, with the aid of a metering pump at a rate of 234 g/h of tallow fatty acid chloride. As a result of the heat of reaction evolved, the temperature rapidly increases to 70° C. The viscosity of the reaction mixture likewise increases substantially. By means of an external heating/cooling circulation, it is ensured that the temperature does not exceed 75° C. After the end of the metering of stearyl chloride, the mixture is stirred for a further 45 minutes at from 65 to 70° C. Thereafter, 20.6 g of concentrated sulfuric acid are slowly added to the reaction mixture, followed by 400 ml of water, and stirring is carried out for 15 minutes at 65° C. After phase separation for 30 minutes, the aqueous phase is discharged. The organic phase is again washed with 250 g of water. After the aqueous phase has separated off, the solvent is distilled off under reduced pressure.

507 g of alkylketene dimer having a lactone content of 85.3% (IR spectroscopic analysis) are obtained.

Comparative Example 3

(Comparison According to EP-A-550 107)

230 g (2.27 mol) of triethylamine are initially taken in the stirred apparatus described in comparative example 2 and are heated to 50° C. 614 g (2.08 mol) of tallow fatty acid chloride are then metered in in the course of 60 minutes. The temperature of the heating circulation is regulated in such a way that the internal temperature does not exceed 65° C. The viscous reaction mixture is stirred for a further 15 minutes at 65° C., 416 ml of a 10% strength hydrochloric acid are then added and stirring is carried out for 15 minutes at 60° C. The stirrer is then switched off. After 15 minutes, the aqueous phase is discharged. 100 g of water are added and the mixture is stirred for 15 minutes at 60° C. The stirrer is then switched off and the aqueous phase is discharged after 30 minutes. The organic phase has a lactone content of about 85.4% (IR spectroscopic analysis).

We claim:

1. A process for the preparation of alkyldiketenes by reacting acyl chlorides with tertiary amines in the absence of solvents with thorough mixing and isolation of the alkyldiketenes from the reaction mixture, wherein acyl chlorides and tertiary amines are reacted in a molar ratio of from 1:1 to 1:1.6 at from 65 to 150° C. and with a residence time of from 1 to 30 minutes, and the viscosity of the reaction mixture is from 300 mPa.s to 100 Pa.s (determined at 60° C. in a Physica rotational viscometer).

2. A process as claimed in claim 1, wherein the viscosity of the reaction mixture is from 500 to 8000 mPa.s (determined at 60° C. in a Physica rotational viscometer).

3. A process as claimed in claim 1, wherein the reactants are thoroughly mixed in static or dynamic mixers.

4. A process as claimed in claim 1, wherein acyl chlorides and tertiary amines are each metered in separately from one another, the reactants are then mixed with one another the reaction mixture is conveyed with the aid of pumps, kneaders or extruders.

5. A process as claimed in claim 1, wherein the reaction is carried out continuously.

6. A process as claimed in claim 1, wherein the reaction is carried out in a twin-screw extruder or in a planetary roller extruder, acyl chlorides and tertiary amines being metered separately from one another and continuously into one of said extruders and the reaction mixture being discharged continuously after passing through the extruder.

7. A process as claimed in claim 1, wherein the reaction is carried out at from 70 to 120° C.

8. A process as claimed in claim 1, wherein the residence time of the reaction mixture in the reactor is from 1 to 15 minutes.

* * * * *